United States Patent [19]

Zeikus et al.

[11] Patent Number: 4,628,031

[45] Date of Patent: Dec. 9, 1986

[54] THERMOSTABLE STARCH CONVERTING ENZYMES

[75] Inventors: Joseph G. Zeikus, Okemos, Mich.; Hyung-Hwan Hyun, Madison, Wis.

[73] Assignee: Michigan Biotechnology Institute, East Lansing, Mich.

[21] Appl. No.: 652,586

[22] Filed: Sep. 18, 1984

[51] Int. Cl.[4] .................. C12N 9/34; C12N 9/44; C12P 19/20; C12P 19/16; C12P 7/14; C12R 1/145

[52] U.S. Cl. ...................... 435/205; 435/96; 435/98; 435/210; 435/162; 435/842

[58] Field of Search ............ 435/96, 98, 161, 162, 435/205, 210, 842

[56] References Cited

U.S. PATENT DOCUMENTS

| | | | |
|---|---|---|---|
| 4,011,139 | 3/1977 | Horwath et al. | 435/210 |
| 4,247,637 | 1/1981 | Tamura et al. | 435/205 |
| 4,335,208 | 6/1982 | Norman | 435/96 |
| 4,400,470 | 8/1983 | Zeikus et al. | 435/162 |
| 4,536,477 | 8/1985 | Katkocin et al. | 435/205 |

OTHER PUBLICATIONS

Zeikus, J. G., A. Ben-Bassat and P. Hegge, 1980, Microbiology of Methanogenesis in Thermal Volcanic Environments, J. Bact. 143: 432–440.

Ng, T. K., A. Ben-Bassat and J. G. Zeikus, 1981, Ethanol Production By Thermophilic Bacteria; Fermentation of Cellulosic Substrates by Co-Cultures of *Clostridium Thermocellum* and *Clostridium Thermohydrosulfuricum*, Appl. Environ. Microbiol. 41: 1337–1343.

Hyun, H. H., J. G. Zeikus, R. Longin, J. Millet and A. Ryter, 1983, Ultrastructure and Extreme Heat Resistance of Spores from Thermophilic Clostridia, J. Bact. 156: 1332–1337.

Zeikus, J. G., 1979, Thermophilic Bacteria: Ecology, Physiology and Technology, Enzyme Microb. Technol. 1: 243–252.

Zeikus, J. G. and T. K. Ng, 1982, Thermophilic Saccharide Fermentations, In: Annual Reports on Fermentation Processes, vol. 5, pp. 63–289, G. Tsao, (ed.), 263–289.

*Primary Examiner*—Lionel M. Shapiro
*Attorney, Agent, or Firm*—Quarles & Brady

[57] ABSTRACT

A thermostable pullulanase and a thermostable glucoamylase are produced by *Clostridium thermohydrosulfuricum*. Methods of producing the enzymes and using them to hydrolyze starch are also disclosed.

3 Claims, 12 Drawing Figures

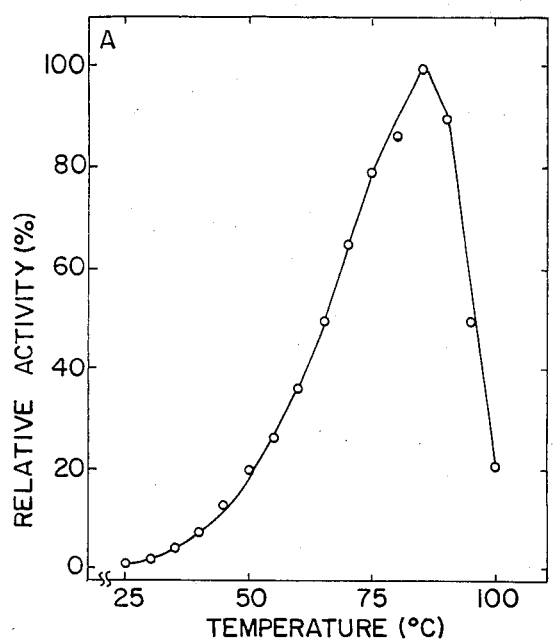
FIG.1A
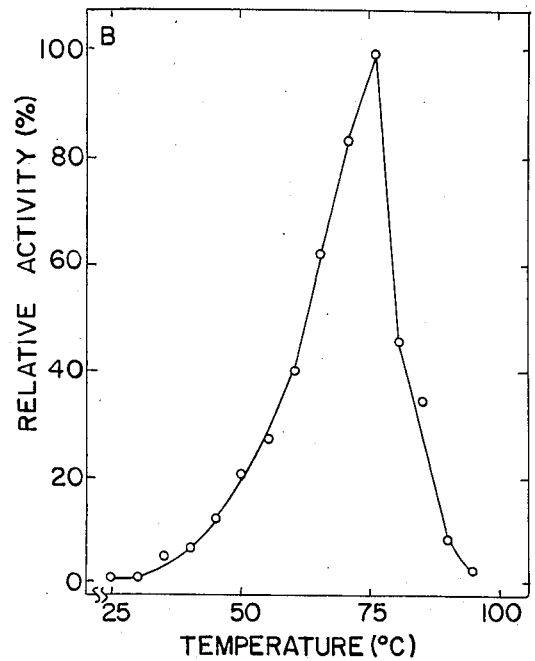
FIG.1B
FIG.2A
FIG.2B
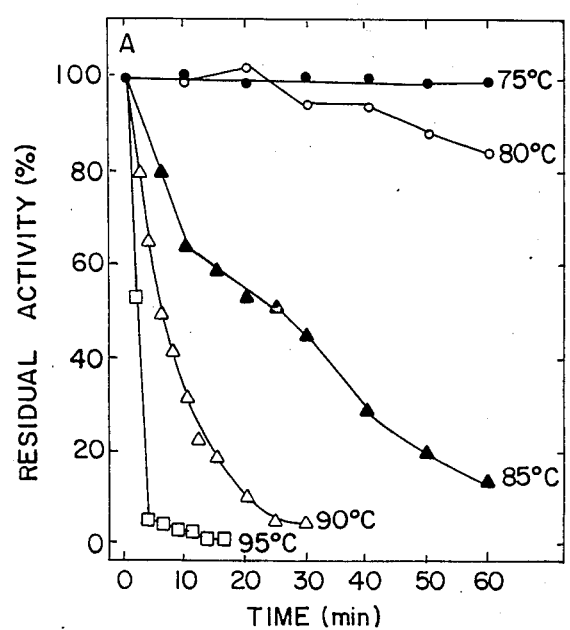
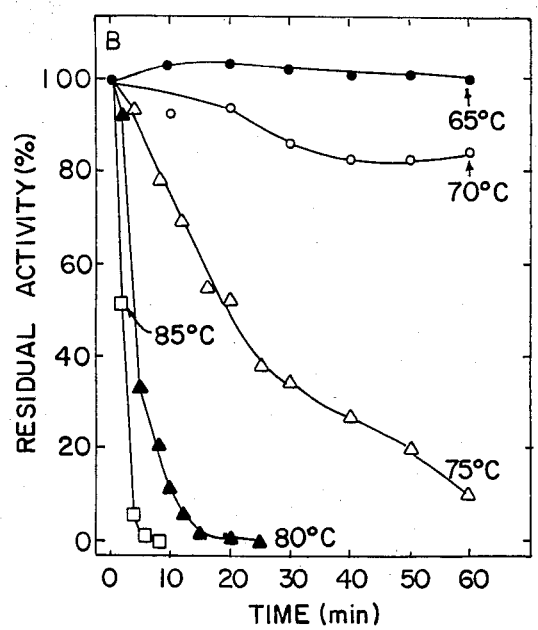

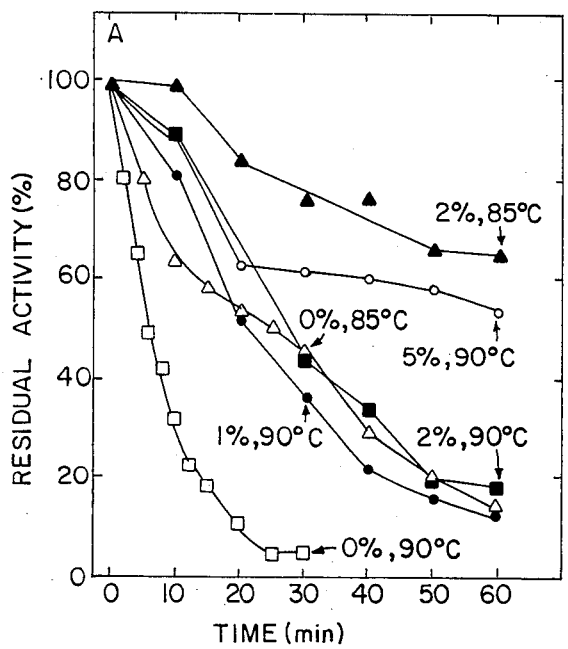
FIG. 3A
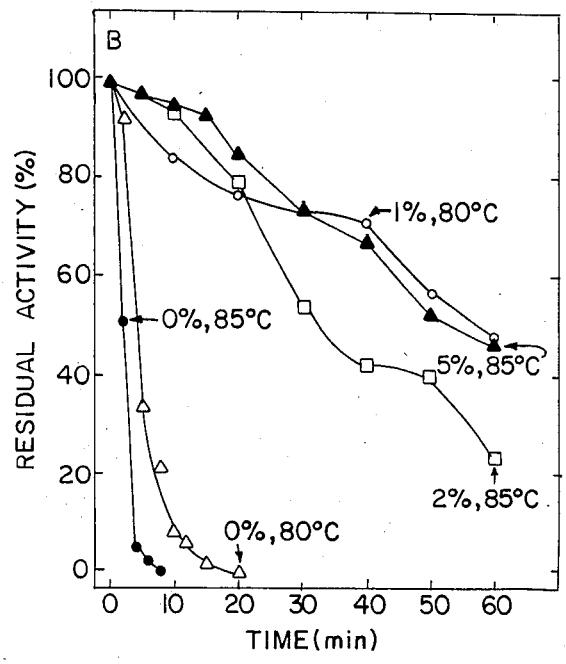
FIG. 3B
FIG. 4A
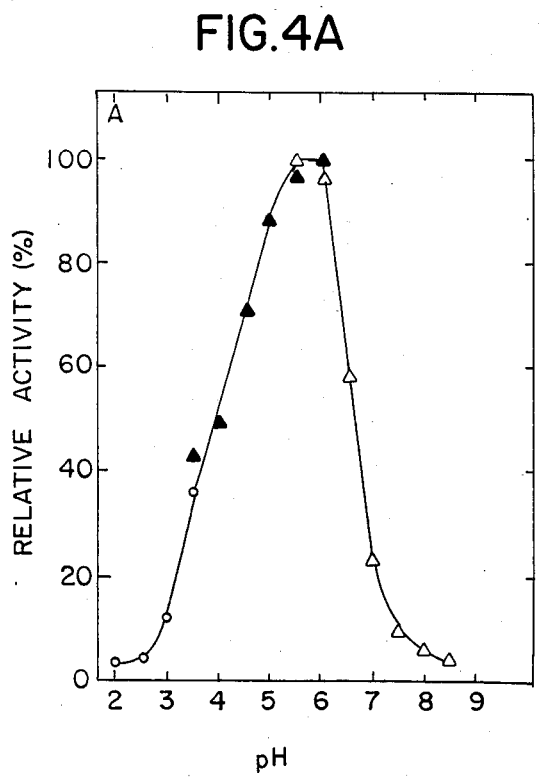
FIG. 4B
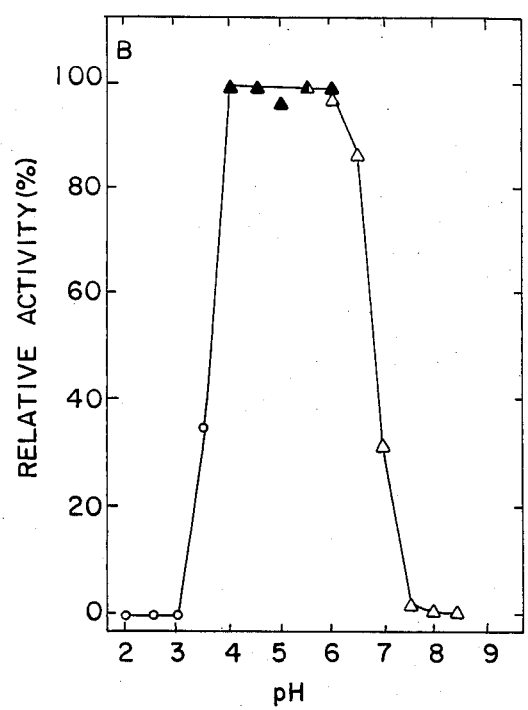

THERMOSTABLE STARCH CONVERTING ENZYMES

FIELD OF THE INVENTION

The present invention relates to enzymes. More particularly, it relates to thermostable starch converting enzymes.

BACKGROUND OF THE INVENTION

A variety of industries (i.e., food, chemical, detergent, textile) employ microbial amylolytic enzymes to convert starch into different sugar solutions. High value is placed on the thermostability and thermoactivity of enzymes for use in the bioprocessing of starch into maltose, glucose, fructose and various sugar syrups.

Glucoamylase (EC 3.2.1.3) is an exo-acting carbohydrate which liberates glucose by hydrolysing α-1,4-linkages consecutively from the non-reducing ends of starch-type substrates. The primary application of glucoamylase is in the production of glucose syrups which can be used for either fermentation, production of crystalline glucose, or as a starting material for production of fructose syrups. The enzyme is produced by bacteria, fungi and yeasts, but fungi are used for commercial enzyme production.

Pullulanase (EC 3.2.1.41) is a debranching enzyme which attacks specifically the α-1,6 glucosidic linkages of starch and pullulan and it is commercially produced using bacteria. This enzyme is generally used in combination with the saccharifying α-amylase or glucoamylase for the production of glucose or conversion syrups because it improves the saccharification rates and yields, and also, in combination with the β-amylases or maltogenic fungal α-amylases for the yield improvement in maltose production.

Commercial starch saccharification processes are usually operated at about 60° C. to promote substrate solubility and to prevent interference by the growth of microorganisms. Both the known glucoamylases and the known pullulanases, however, are unstable at temperatures above 60° C. Thus, the practical utility of known pullulanases or glucoamylases are somewhat restricted due to their thermal instability. Therefore, the discovery of an inexpensive source of active, thermostable glucoamylase and/or pullulanase would be an important contribution to the starch processing industry.

To date, essentially, nothing is known about the biochemical attributes of thermophilic bacteria that actively ferment starch to ethanol at temperatures of about 60° C. or higher. From our earlier work we do know, however, that thermoanaerobic bacteria can often process at faster metabolic rates and produce more thermostable enzymes than mesophilic microorganisms.

SUMMARY OF THE INVENTION

We recently discovered that the microorganism *Clostridium thermohydrosulfuricum* produces both a glucoamylase and a pullulanase which have unique and valuable thermoactive and thermostable characteristics.

The enzymes are produced by culturing thermostable glucoamylase and pullulanase producing *Clostridium thermohydrosulfuricum* on a nutrient broth under anaerobic conditions until enzymatic activity is detectable and thereafter isolating the thermostable glucoamylase and pullulanase by conventional means.

The primary objects of the present invention are to disclose and describe the glucoamylase and pullulanase produced by *C. thermohydrosulfuricum*, the methods by which they are prepared and methods employing them. Further objects of the invention will be apparent to those skilled in the art from the description and drawings.

BRIEF DESCRIPTION OF THE DRAWINGS

FIG. 1 shows the dependence of pullulanase (A) and glucoamylase (B) activity on temperature. Both enzymes were assayed using 10 μl cell extract (20.8 mg protein/ml) for glucoamylase and 7 μl cell extract to pullulanase. 100% activity corresponds to 0.18 units/mg protein for glucoamylase and 1.96 units/mg protein for pullulanase.

FIG. 2 shows the thermal stability of pullulanase (A) and glucoamylase (B) in the absence of substrate. Cell extracts (4.2 mg protein/ml) in 0.1M sodium acetate buffer (pH 5.0) were incubated at stated temperatures and the residual activities were assayed. Maximum activity was 0.076 units/mg protein for the glucoamylase at pH 4.8 and 60° C.; and 0.71 units/mg protein for the pullulanase at pH 6.0 and 60° C.

FIG. 3 shows the effect of starch on thermal stability of pullulanase (A) and glucoamylase (B) of *C. thermohydrosulfuricum*. Reaction mixtures (5 ml) containing 0.5 ml cell extract (20.8 mg protein/ml), 0.1M sodium acetate buffer (pH 5.0) and the appropriate amount of soluble starch were incubated at the stated temperatures, and the residual activities were assayed. Maximum activity was 0.076 units/mg protein for glucoamylase at pH 4.8 and 60° C., and 0.71 units/mg protein for pullulanase at pH 6.0 and 60° C.

FIG. 4 shows the dependence of pullulanase (A) and glucoamylase (B) activity on pH. Both enzymes were assayed at 60° C. using 0.1M of glycine-HCl (-o-), Na-acetate (-▲-), and Na-phosphate (-Δ-) buffer. Assays used 20 μl cell extract (20.8 mg. protein/ml) for pullulanase, and 30 μl cell extract for glucoamylase. Maximum activity was 0.71 units/mg protein for pullulanase at pH 6.0 and 60° C., and 0.076 units/mg protein for glucoamylase at pH 4.8 and 60° C.

DESCRIPTION OF PREFERRED EMBODIMENT

Figure 5A:
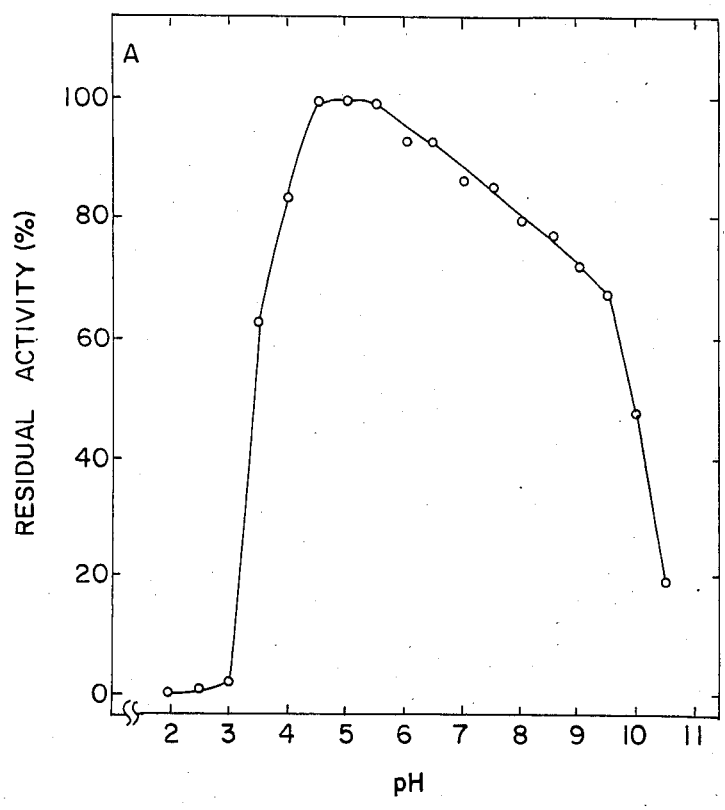
FIG. 5 shows the pH stability of pullulanase (A) and glucoamylase (B) in the absence of starch. Enzyme solutions (4.2 mg protein/ml) were prepared in either 0.1M glycine-HCl (-o-), Na-acetate (-▲-), Na-phosphate (-Δ-) or glycine-Na (-●-) buffer for glucoamylase or in a combined buffer that contained 50 mM of each buffer for pullulanase and they were incubated at 60° C. for 1 hr prior to analysis of residual activity. Maximum activity was 0.71 units/mg protein for pullulanase at pH 7.5 and 60° C., and 0.076 units/mg protein for glucoamylase at pH 4.8 and 60° C.

In the preferred practice of the present invention, a thermostable glucoamylase and/or thermostable pullulanase producing Clostridium thermohydrosulfuricum having the identifying characteristics of ATCC 33223 is cultured in a nutrient medium containing starch and essential vitamins, minerals and growth factors until substantial enzymatic activity is detectable and then the enzymes are isolated by conventional means.

MATERIALS AND METHODS

Chemicals. All chemicals were reagent grade and obtained from either Mallinckrodt (Paris, KY, USA) or Sigma Chemical (St. Louis, MO, USA). The $N_2CO_2/(95:5)$ gas was obtained from Matheson (Joliet, IL, USA), and purified free of oxygen by passage over the heated (37° C.) copper filings.

Organism and cultivation. C. thermohydrosulfuricum strain 39E was isolated form Octopus Spring in Yellowstone National Park (1) and it was deposited in the American Type Culture Collection, Rockville, MD, USA (ATCC 33223). Stringent anaerobic culture techniques (1) were employed for medium preparation and cultivation. The organism was routinely grown at 65° C. in 26 ml anaerobic pressure tubes (Bellco Glass Co., Vineland, NJ, USA) that contained 10 ml of TYE medium (2) with 0.5% glucose or soluble starch and $N_2CO_2$ (95:5) gas headspace. Culture media were autoclaved for 45 min to assure killing the extremely heat resistant spores of thermoanaerobes (3).

For determination of starch hydrolysis reaction on petri dishes, the organism was center streaked in an anaerobic chamber (Coy Products, Ann Arbor, MI, USA) onto plates of TYE medium that contained 1.0% soluble starch and 3.0% purified agar (Difco). The plates were placed into an anoxic paint can (W. R. Brown Division Intermatic, Spring Grove, IL) under nitrogen incubated at 60° C. for 4 days. The plates were removed from the paint can and flooded with iodine solution (1% $I_2$ and 2% KI in $H_2O$) and hydrolysis zones were visually observed.

Preparation of enzyme. For preparation of the washed cells and culture supernatant, the organism was grown on TYE medium with 0.5% soluble starch until the stationary phase (24 h) and the culture was centrifuged at 12,000×g for 10 min. The supernatant was decanted and the cells were washed twice with 20 mM sodium acetate buffer, pH 6.0 and resuspended in the same buffer. For preparation of the cell extracts, the organism was mass cultured in a 14 liter fermentor (New Brunswick Scientific Co., New Brunswick, NJ) that contained 10 liters of TYE medium with 0.5% soluble starch, at 65° C. with $N_2/CO_2$ (95:5) gassing (200 ml/h). The cells were harvested at late exponential phase by centrifugation with a DuPont (Wilmington, DE) KSB continuous-flow centrifugation system. Cell extracts were prepared aerobically by suspended 3 g of wet cell paste in 100 ml of 20 mM sodium acetate buffer (pH 6.0) followed by passage through a French pressure cell at 20,000 lb/in$^2$. The supernatant was collected by centrifugation at 30,000×g for 30 min at 4° C. and was used for analysis of amylase activity. Protein concentration was determined by the Lowry method.

Enzyme assays. Amylase activity (i.e., reducing sugar production from starch) was measured in reaction mixtures that consisted of 1 ml of soluble starch (10%), 1 ml of 0.5M sodium acetate buffer, (pH 6.0) and 3 ml of the enzyme source diluted with water. After incubation at 60° C. for 30 min, the reaction was stopped by immediate cooling in an ice bath and reducing power was then quantified by the dinitrosalicylic acid method.

Pullulanase activity was measured by incubating a reaction mixture (1 ml) that consisted of 1% pullulan in 0.1M sodium acetate buffer (pH 6.0) and the enzyme source at 60° C. for 30 min. The reaction was stopped by immersing the reaction tubes in an ice bath and adding 4 ml of the cooled 3,5-dinitrosalicylic acid. One unit of amylase or pullulanase activity is defined as the amount of enzyme which released 1 μmol of reducing sugar with glucose as standard per min under the described conditions.

Glucoamylase activity was measured in reaction mixtures (1 ml) that consisted of 1% soluble starch in 0.1M sodium acetate buffer (pH 4.8) and the enzyme source. After incubating at 60° C. for 30 min, the reaction mixtures were boiled in a steam bath for 10 min, and centrifuged to remove the insoluble materials. The released glucose was estimated by the hexokinase and glucose-6-phosphate dehydrogenase method. One unit of glucoamylase is defined as the amount of enzyme that produced one μmol of glucose per min under the assay conditions.

Analysis of starch and pullulan hydrolysis products. High pressure liquid chromatography (HPLC) and a paper chromatographic method were employed for the qualitative analysis of reaction products in starch or pullulan hydrolysates. A Perkin Elmer Series B liquid chromatograph equipped with a Sima 10 data station (Perkin Elmer Corp., Norwalk, CT) was used for the HPLC analysis. Reaction products were separated on a Biorad Oligosaccharide Analysis Column (300×7.8 mm, Aminex HPX-42A) fitted with a microguard precolumn (40×4.6 mm, packed with Aminex HPX-85C, Biorad Lab, Richmond, CA). The enzyme hydrolysates were centrifuged at 5,000×g and loaded onto the column. Degassed double distilled water was used as the mobile phase with a flow rate of 0.6 ml/min at ambient temperature. Paper chromatographic analysis employed the methods described by Glymph and Stutzenberger (4).

Quantitative analysis of glucose and reducing sugar in the enzymatic starch hydrolysates was performed by the same procedures as described above for enzyme assays. Total carbohyrate was assayed by the phenolsulfuric acid method.

RESULTS

Location and types of amylase activities. In preliminary experiments, large clear zone (3 cm in diameter) appeared around colonies grown on starch agar plates which were stained with iodine. This result implied that C. thermohydrosulfuricum produced amylases capable of completely hydrolyzing starch but, it could not differentiate whether these activities were cell bound or extracellular.

Table 1 summarizes the results of experiments demonstrating the cellular location of different amylases activities in C. thermohydrosulfuricum. The organism contained a cell bound glucoamylase activity and a pullulanase activity in exponential phase cultures. After long incubation in the stationary growth phase (20 h), these activities were released into the medium due to rapid cell lysis. It was not possible by this analysis, however, to demonstrate α-amylase activity because the reducing sugar-producing amylase activity observed was almost negligible and it was close to the sum of measured glucoamylase and pullulanase activity.

TABLE 1

Amylolytic Enzyme Activities and Cellular Location in C. thermohydrosulfuricum

| Enzyme | Assay Condition | Activity-Location | | |
|---|---|---|---|---|
| | | Supernatant (U/ml) | Washed Cells (U/ml) | Cell-Free Extracts (U/mg-protein) |
| Amylase | Aerobic | 0.00 | 0.21 | 0.42 |
| | Anaerobic | 0.00 | 0.21 | 0.42 |
| Pullulanase | Aerobic | 0.00 | 0.17 | 0.27 |
| | Anaerobic | 0.00 | 0.17 | 0.27 |
| Glucoamyase | Aerobic | 0.00 | 0.03 | 0.04 |
| | Anaerobic | 0.00 | 0.03 | 0.04 |

<sup>a</sup>C. thermohydrosulfuricum was grown on TYE medium that contained 0.5% soluble starch at 65° C. until the late logarithmic growth phase. Anaerobic assay conditions were established via addition of dithiothreitol (2 mM) and gassing with $N_2$ gas to prepare all enzyme assay components. Pullulanase activity was assayed by incubating 1% pullulan solution in 0.1 M phosphate buffered, pH 7.0, at 60° C. for 30 min.

In order to confirm the presences of pullulanases and glucoamylase, starch and pullulan were treated with cell extract and the hydrolysis products were analyzed by either HPLC or paper chromatography methods. These reaction mixtures (20 ml) contained 1% substrate in 0.1M sodium acetate buffer, 2 units of enzyme and were incubated at 75° C. Pullulan was readily hydrolyzed and within 1 hour only maltotriose was observed but after 3 hours of incubation, glucose was also detected. Starch was also readily hydrolyzed but with glucose as the main product. After 24 hours incubation, 80% of the starch was converted into glucose.

Physiochemical properties of amylase activities. The relation of temperature to amylase stability and activity were examined in detail. FIG. 1 illustrates that both pullulanase and glucoamylase were active in a broad temperature range (i.e., 35°–90° C.) and displayed temperature optima for activity at 85° and 75° C., respectively. When Arhennious plots of specific activity versus 1/Temperature were determined (data not shown), $Q_{10}$ values of 1.8 and 2.10 were calculated for pullulanase and glucoamylase, respectively.

The effect of temperature on the heat stability of amylases in the absence of substrates is shown in FIG. 2. Under these conditions, pullulanase activity was entirely stable at 75° C. for 60 min; whereas, glucoamylase was almost entirely destroyed. Both amylase activities were destroyed by treatment at 85° C. but inhibition of enzyme activity was more rapid for glucoamylase.

As shown in FIG. 3, the thermal stability of amylase activities were greatly enhanced by the presence of substrates. Starch provided protection from heat inactivation for both pullulanase and glucoamylase; and, this effect was substrate concentration dependent for both enzymes. In the presence of 5% starch, pullulanase activity was completely stable at 85° C. and 55% of activity was detected after treatment at 90° C. for 1 hour. On the other hand, glucoamylase in the presence of 5% starch was completely stable at 75° C. and 50% activity was retained after treatment at 85° C. for 1 hour.

Figure 5B:
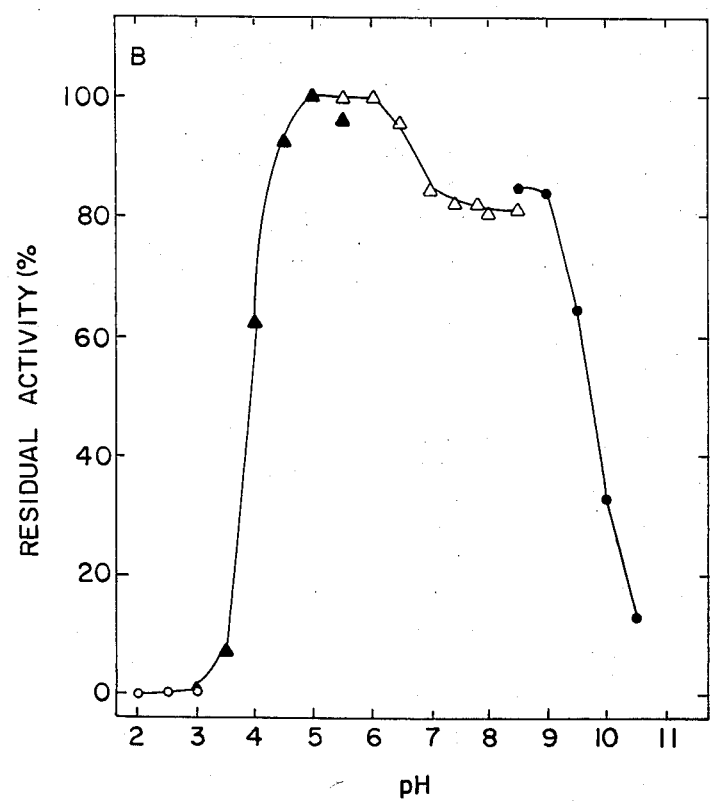

Both pullulanase and glucoamylase displayed a similar broad pH range for activity (pH 3.5–7.0) or stability (pH 4.0–9.0) (FIGS. 4 and 5). The optimum pH for activity of pullulanase and glucoamylase was 5.5–6.0 and 4.0–6.0, respectively. Under the assay conditions employed, pullulanase and glucoamylase were entirely stable from 4.5 to 5.5 and 5.0–6.0, respectively.

The effects of ethanol on enzyme stability and activity was examined using the following conditions. Cell extract (20 units/ml of pullulanase or 2.6 units of glucoamylase) in 0.1M sodium acetate buffer (pH 5.5) was treated at 65° C. with varying concentrations of ethanol. Samples were withdrawn at time intervals and residual amylase activity was determined. Both enzymes were not inactivated by treatment with 10% (v/v) ethanol for one hour. The direct addition of 3% (v/v) ethanol to reaction mixtures did not alter amylase activity. In the presence of 10% (v/v) ethanol, however, pullulanase and glucoamylase activities were decreased by 20% indicating precipitation of polymeric substrate rather than inhibition of enzyme per se.

Figure 6:
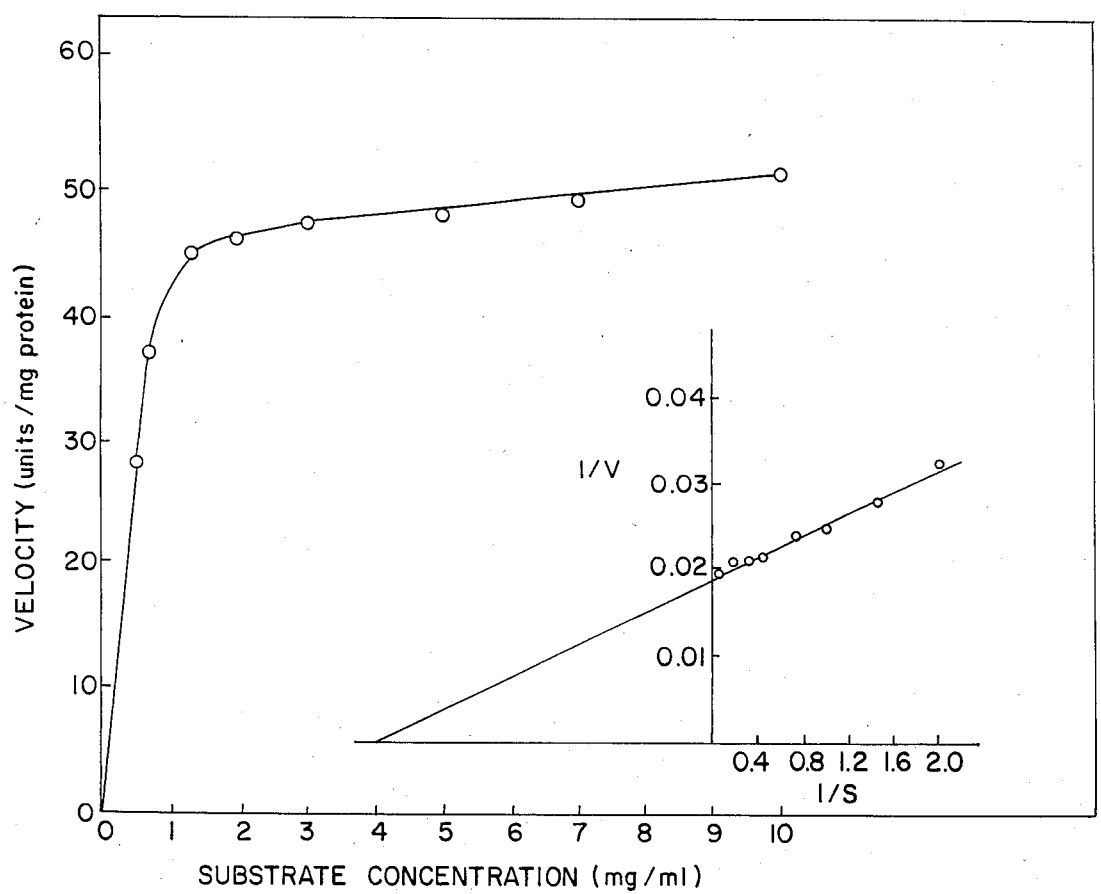
FIG. 6 shows the kinetic properties of the pullulanase from *C. thermohydrosulfuricum*. Reaction mixtures contained 0.1M acetate buffer (pH 6.0), enzyme (0.2 mg protein/ml), and the appropriate amount of pullulan and were incubated at 65° C. Samples were withdrawn at various intervals to measure the initial velocity of total reducing sugar formation.

Kinetic properties of amylase activities. The apparent kinetic constants were determined for pullulanase and glucoamylase activity by determination of product formation rate versus time curves. FIG. 6 demonstrates that the dependence of the rate of enzymatic pullulan hydrolysis on the substrate concentration followed Michaelis-Menten kinetics and that linear relationships of I/V versus I/[S] were obtained. The apparent $[S]_{0.5}V$ and Vmax as determined from the double reciprocal were 0.33 mg/ml and 2.6 units/mg protein.

Figure 7:
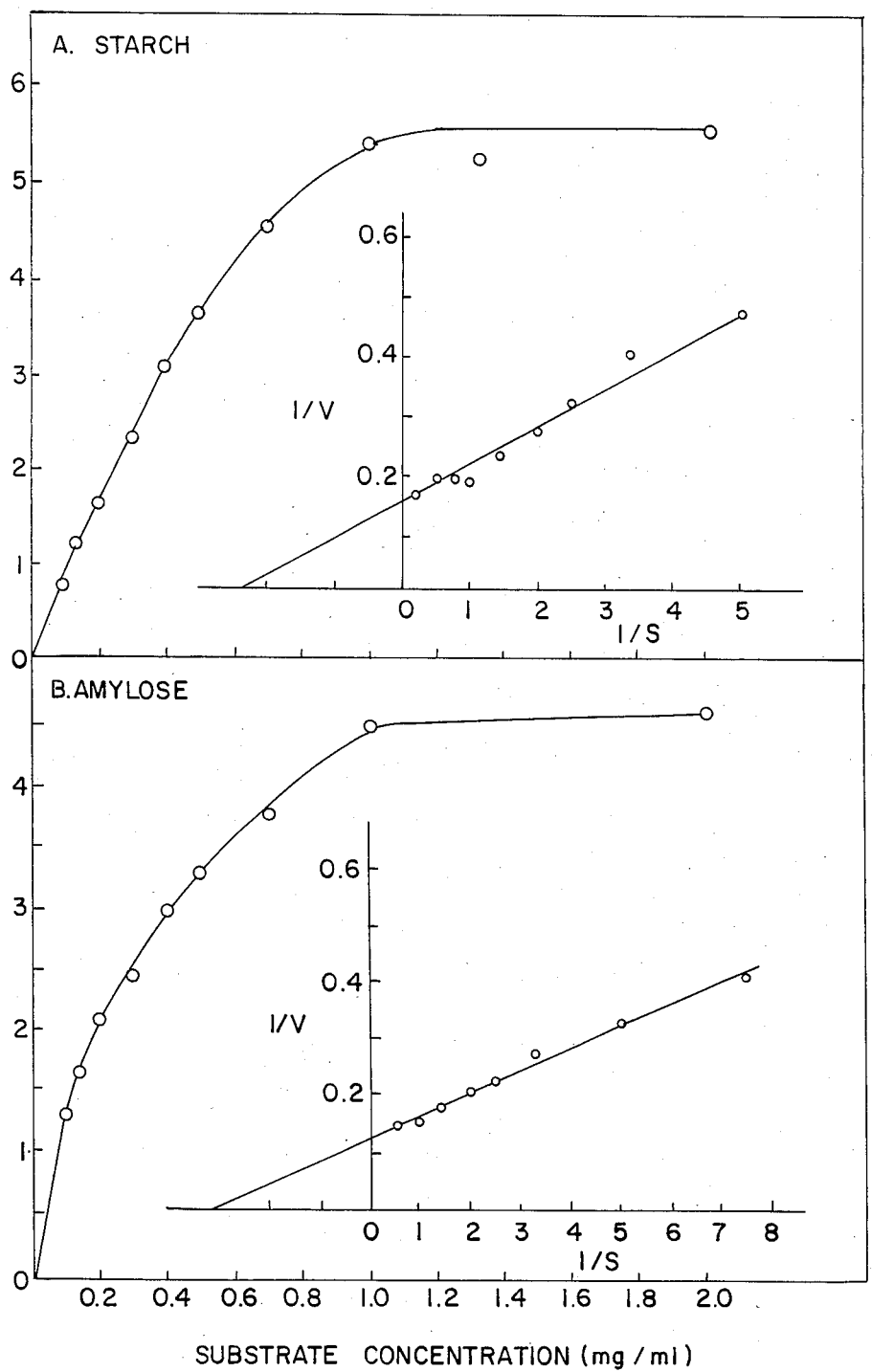
FIG. 7 shows the kinetic properties of the glucoamylase from *C. thermohydrosulfuricum* on starch versus amylose. Reaction mixtures contained 0.1M acetate buffer (pH 4.8) enzyme (0.3 mg protein/ml), the appropriate amount of substrate and were incubated at 65° C. Samples were withdrawn at various intervals to measure the initial velocity of glucose formation.

FIG. 7 compares the relationships between glucoamylase activity and starch or amylase concentration. Again, the enzyme activity displayed standard Michaelis-Menten kinetics; and, the apparent Vmax and Km values determined from double reciprocal plots were: 0.31 U/mg protein and 0.41 mg/ml with starch as substrate or 0.26 U/mg protein and 0.32 mg/ml for amylose.

DISCUSSION

In general, the foregoing data establishes that C. thermohydrosulfuricum produces both a pullulanase and a glucoamylase, both of these enzymes have similar pH optima and high thermal stability which make them useful for industrial applications (5).

It also is of interest that active and complete hydrolysis of starch into glucose at temperatures greater than 60° C. by C. thermohydrosulfuricum is achieved by the pullulanase and the glucoamylase. In contrast, the starch degradation mechanisms by aerobic mesophiles or thermophiles are generally associated with active α-amylase production. This is not the case for starch transformation by C. thermohydrosulfuricum.

The extremely high temperature values observed for optimal enzyme activity of the pullulanase (85° C.) and the glucoamylase (75° C.) are unusual. The reported temperature optima of pullulanse and isoamylases obtained from plants or other microorganisms are below 60° C. The temperature optima of glucoamylases generally fall in the range of 40° to 60° C., except for Humicola lanuginosa glucoamylase II with optimal activity near 65° C. The extreme thermal stability of the pullulanase (up to 85° C.) and glucoamylase (up to 75° C.) are perhaps the highest values reported for these types of enzymes. The pullulanases from Aerobacter and Bacillus species are stable below 50° C. while enzymes from Streptococcus and Streptomycete species are stable below 40° C. Most of the known glucoamylases are unstable above 60° C. Therefore, both the pullulanase and the glucoamylase of C. thermohydrosulfuricum are outstanding in terms of thermostability and activity at high temperatures.

The optimal pH for enzyme activity and the pH range for enzyme stability of C. thermohydrosulfuricum glucoamylase and pullulanase are in the general range reported for other sources of these enzymes. For example, the pH optima for most glucoamylases and pullulanases are 4.5 to 5.4 and 5.0 and 5.8, respectively. Likewise, pullulanase and glucoamylase from other sources are also stable between 4.5-5.5 and 5.0-6.0, respectively. Notably, both the pullulanase and glucoamylase of *C. thermohydrosulfuricum* display high activity and stability in similar temperature and pH ranges.

If it is desired to obtain a pullulanase free of glucoamylase, it can be obtained by heat treating a mixture of the enzymes at about 80° C. to about 90° C. to inactivate the glucoamylase.

It will be appreciated by those skilled in the art that enzyme yield may be enhanced through mutation of the organism or genetic recombination techniques. Therefore, the scope of the invention should not be limited to the specific strain of organism described above because any organism capable of producing a thermostable glucoamylase and/or pullulanase similar to those produced by *C. thermohydrosulfuricum* having the identifying characteristics of ATCC 33223 can be used.

REFERENCES

1. Zeikus, J. G., A. Ben-Bassat and P. Hegge. 1980. Microbiology of methanogenesis in thermal volcanic environments. J. Bact. 143: 432–440.
2. Ng, T. K., A. Ben-Bassat and J. G. Zeikus. 1981. Ethanol production by thermophilic bacteria; fermentation of cellulosic substrates by co-cultures of *Clostridium thermocellum* and *Clostridium thermohydrosulfuricum*. Appl. Environ. Microbiol. 41: 1337–1343.
3. Hyun, H. H., J. G. Zeikus, R. Longin, J. Millet and A. Ryter. 1983. Ultrastructure and extreme heat resistance of spores from thermophilic clostridia. J. Bact. 156: 1332–1337.
4. Glymph, J. L. and F. J. Stutzenberger. 1977. Production, purification, and characterization of α-amylase from *Thermomonospora curvata*. Appl. Environ. Microbiol. 34: 391–397.
5. Zeikus, J. G. 1979. Thermophilic bacteria: ecology, physiology and technology. Enzyme Microb. Technol. 1: 243–252.
6. Zeikus, J. G. and T. K. Ng. 1982. Thermophilic saccharide fermentations. In: Annual Reports on Fermentation Processes, Vol. 5, p. 263–289. G. Tsao, (ed.).

The above references are incorporated by reference herein.

We claim:

1. A method of producing a thermostable glucoamylase and a thermostable pullulanase which comprises anaerobically culturing a thermostable glucoamylase and pullulanase producing *Clostridium thermohydrosulfuricum* in a nutrient medium until substantial enzymatic activity is detectable and thereafter isolating the glucoamylase and pullulanase.

2. A thermostable glucoamylase from *Clostridium thermohydrosulfuricum* having the following physiochemical properties:
   (1) Reactivity: It reacts with starch allowing complete transformation to glucose;
   (2) Substrate specificity: It reacts with any substrate with α-1,4 glycosidic bonds;
   (3) Optimum pH value: It is about 4.0 to about 6.0;
   (4) pH stability: It is stable from about 5.0 to about 6.0;
   (5) Optimum temperature: It is about 75° C.;
   (6) Temperature stability: It is not stable and can be deactivated above about 65° C. in the absence of substrate but is stable to about 75° C. in the presence of substrate; and
   (7) Influences of inhibitors: It is not inhibited by perchloricmercuric benzoate, $Ca^{++}$ and ethanol.

3. A thermostable pullulanase from *Clostridium thermohydrosulfuricum* having the following physiochemical properties:
   (1) Reactivity: It reacts with starch to form dextrine by debranching;
   (2) Substrate specificity: It reacts with carbohydrates with α1,6 glycosidic bonds;
   (3) Optimum pH value: It is about pH 5.5 to about pH 6.0;
   (4) pH stability: It is from about pH 4.5 to about pH 5.5;
   (5) Optimum temperature: It is about 85° C.;
   (6) Temperature stability: It is stable at about 75° C. in the absence of substrate and to about 85° C. in the presence of substrate;
   (7) Influences of inhibitors: It is not inhibited by perchloricmercuric benzoate or ethanol.

* * * * *